United States Patent [19]

Ueno et al.

[11] Patent Number: 4,966,992

[45] Date of Patent: Oct. 30, 1990

[54] PROCESS FOR PRODUCTION OF AROMATIC HYDROXYCARBOXYLIC ACID

[75] Inventors: Ryuzo Ueno, Nishinomiya; Yoshiyasu Masada, Hirakata; Yoshihiko Kuwae; Keiji Kawata, both of Nishinomiya, all of Japan

[73] Assignee: Kabushiki Kaisha Ueno Seiyaku Oyo Kenkyujo, Osaka, Japan

[21] Appl. No.: 298,135

[22] Filed: Jan. 18, 1989

[30] Foreign Application Priority Data

Jan. 23, 1988 [JP] . Japan .................................. 63-13437

[51] Int. Cl.$^5$ .............................................. C07C 51/15
[52] U.S. Cl. ..................................... 562/424; 562/425
[58] Field of Search ................................ 562/424, 425

[56] References Cited

U.S. PATENT DOCUMENTS

| | | | |
|---|---|---|---|
| 1,725,394 | 8/1929 | Dieterle | 562/424 |
| 4,287,357 | 9/1981 | Mueller et al. | 562/424 |
| 4,345,095 | 8/1982 | Mueller et al. | 562/424 |

FOREIGN PATENT DOCUMENTS

| | | |
|---|---|---|
| 226705 | 2/1958 | Australia . |
| 878534 | 8/1971 | Canada . |
| 0066205 | 12/1982 | European Pat. Off. . |
| 0089564 | 2/1983 | European Pat. Off. . |
| 0254596 | 1/1988 | European Pat. Off. . |
| 298289 | 1/1989 | European Pat. Off. . |
| 1205447 | 9/1970 | United Kingdom . |

*Primary Examiner*—Paul J. Killos
*Attorney, Agent, or Firm*—Sughrue, Mion, Zinn, Macpeak & Seas

[57] ABSTRACT

The present invention provides a method of production of aromatic hydroxycarboxylic acids by the reaction of alkaline metal salts of phenols or naphthols with carbon dioxide, in which free phenols or free naphthols produced as by-products in the reaction system are removed from the system so as to control the content of free phenols or free naphthols at a suitable level, by which a purer objective compound can be obtained at high yield under the condition of lower temperature and shorter time.

8 Claims, No Drawings

PROCESS FOR PRODUCTION OF AROMATIC HYDROXYCARBOXYLIC ACID

BACKGROUND OF THE INVENTION

The present invention relates to a process for production of aromatic hydroxycarboxylic acids.

Aromatic hydroxycarboxylic acids are important for raw materials or intermediates for antiseptics, antifungals, pigments, dyes, liquid crystals, pharmaceuticals, agricultures and the like, which are generally produced by the reaction of alkaline metal salts of phenolic or naphtholic compounds with carbon dioxide.

As such a method a solid-vapor phase reaction called as Kolbe-Schmitt reaction has been used, but it has many problems attributed to the solid-vapor phase reaction, for instance, a long reaction time, a great loss of raw materials by side-reaction which is caused by a thermal unevenness, an inconstant yield due to difficulty in reaction control and so on. Various improvements proposed to solve the above problems have not satisfied industrial requirements.

Japanese Patent Publication No. 9529/1970 (corresponding to U.S. Pat. No. 3,816,521) discloses a method of continuous production of p-hydroxybenzoic acid by the reaction of phenol and carbon dioxide, in which as a phenolic compound potassium salt of phenol and free phenol are used in a given ratio dispersed in a specific reaction medium such as aliphatic hydrocarbons, aromatic hydrocarbons and the like, but it does not refer to the removal of byproducts from the reaction system as a vapor. Japanese Patent Publication No. 53296/1981 (corresponding to U.S. Pat. No. 4,239,913) discloses the production of 2-hydroxynaphthalene-3-carboxylic acid by the reaction of sodium salt of β-naphthol with carbon dioxide, in which the reaction is carried out in the dispersion of mixture of the sodium salt and β-naphthol in a specific reaction medium such as a light oil in a given ratio. This method does not refer to the removal of by-products produced during the reaction as a vapor from the reaction system, either. The both methods are based on the fact that the mixture of a free phenolic or naphtholic compound and its alkaline metal salt in a specific ratio can be maintained liquid at a reaction temperature, and the contact of the salts with the carbon dioxide is advantageously achieved in the dispersion of the alkaline metal salts in a specific reaction medium. According to these methods there are improved in productivity, purity of aromatic hydroxycarboxylic acid produced, yield as well as the reaction can be continuously operated and completed within short time.

As apparent from the above the mixture of the phenol (naphthol) and its alkaline metal salts in the reaction medium (such a mixture is referred to as a reaction mixture through the present specification, and the alkaline metal salts alone in the reaction medium is also referred to a reaction mixture) should be maintained in a specified component ratio over the reaction process, but the amount of free phenols or free naphthols discharged from the reaction system is practically depended on the amount of the reaction medium. Therefore, these both processes still have following difficulties:

(1) If the reaction mixture is maintained for a long time in the reaction system, free phenols or free naphthols produced during the reaction accumulate more than the specified ratio in the reaction system so as to be beyond the suitable ratio, and then by-products such as tars from phenols, naphthols and the like are still liable to increase; and (2) If excess amount of phenols or naphthols is discharged to decrease the by-products, the amount of the reaction medium relatively increases, and the residence time of the reaction mixture becomes shorter, so that the conversion ratio from alkaline metal salts of phenols (naphthols) to the corresponding hydroxycarboxylic acids decreases.

Additionally, as, when a batch reaction is used, it has naturally no means to discharge the phenols or naphthols produced during the reaction in these methods, the specified ratio of the reaction mixture cannot be suitably maintained. Therefore, higher yield cannot be expected.

SUMMARY OF THE INVENTION

The object of the present invention is to provide an aromatic hydroxycarboxylic acid with higher purity and in a higher yield at a lower temperature for a shorter reaction time. In order to achieve the above object the component ratio in the reaction mixture is maintained within a suitable range, for which alkaline metal salts of phenols or naphthols are reacted with carbon dioxide under the condition that the alkaline metal salts of the phenols or naphthols are melted in the presence of reaction medium as removing by-products produced during the reaction as a vapor. This is more effectively achieved by dispersing the carbon dioxide gas into the reaction mixture to enhance the vapor-liquid contact. This process can be applied to a batch reaction and a continuous reaction, and excellent results can be obtained in the each reaction.

DETAILED DESCRIPTION OF THE INVENTION

The present invention relates to a process for production of an aromatic hydroxycarboxylic acid, in which alkaline metal salts of phenols or naphthols selected from the group consisting of sodium phenolates, potassium phenolates, sodium α-naphtholates, potassium α-naphtholates, sodium β-naphtholates are reacted with carbon dioxide under such a condition that said alkaline metal salts of phenols or naphthols are melted in the presence of a reaction medium as removing by-products produced during the reaction as a vapor.

The process of the present invention is carried out in the presence of a reaction medium substantially stable at a reaction temperature of the alkaline metal salts of the phenols or naphthols with carbon dioxides.

The alkaline metal salts of phenols and naphthols of the present invention may include sodium phenolate, potassium phenolate, sodium β-naphtholate, sodium α-naphtholate, potassium α-naphtholate and the like. These may include salts of phenols or naphthols having at least one substituent on the aromatic ring. The example of the substituent is a halogen atom such as a fluorine atom, a bromine atom, and a chlorine atom; an alkyl group such as methyl, ethyl, propyl and the like; an alkoxy group such as methoxy, ethoxy and the like; and others such as nitro, sulfonyl, amino, phenyl, benzyl and the like.

In order to melt the alkaline metal salts of phenols or naphthols in the presence of the reaction medium the temperature of reaction medium (i.e. reaction temperature) may be raised over the melting point of the salts.

In case that the melting point of alkaline metal salts of the phenols or naphthols is higher than a desirable reaction temperature or a lower reaction temperature is desirably employed, the corresponding free phenols or free naphthols may be added to the salts so as to lower the melting point of the mixture to a desirable temperature. Such a mixture is extremely preferable because the salts, the liquid phase of the free phenols or free naphthols and the reaction medium form an excellent dispersion.

The alkaline metal salts of the phenols or naphthols or the mixture of these salts and free phenols or free naphthols be sufficiently dehydrated. Such dehydrated salts can be easily prepared from phenols or naphthols and their alkaline alkali metal salts according a usual manner. The reaction mixture may be dehydrated by, for example, suspending the alkaline metal salts containing water into the reaction medium and heating the suspension with blowing an inert gas such as nitrogen gas into the suspension. The dehydration may be made at any stage of the preparation of the reaction mixture containing alkaline metal salts of phenols or naphthols and, if necessary, free phenols or free naphthols. Any dehydration process may employed, for instance, use of dehydrating agents.

In order to practise the present invention the alkaline metal salts of the phenols or naphthols should be melted in the reaction medium. In a preferable embodiment, as aforementioned, corresponding free phenols or free naphthols are allowed to constantly exist in the reaction mixture. A preferable ratio of the alkaline metal salts of the phenols or naphthols to free phenols or free naphthols is one mole to 0.05–3 mole, more preferably one mole to 0.1–3 mole, most preferably one mole to 0.2–2 mole. In any known methods any specific means to remove excess free phenols or free naphthols produced during reaction from a reaction system as a vapor is not employed. Therefore, such excess phenols or naphthols are accumulated in the reaction mixture, so that the ratio of the free phenols or free naphthols to the alkaline metal salts of the phenols or naphthols increases to give rise to a side-reaction or a tar formation, as the result of which yield and selective ratio of the objective compounds decrease.

The reaction of the alkaline metal salts of phenols or naphthols with carbon dioxide may be carried out at or more than 150° C., preferably 160°–300° C., under carbon dioxide pressure of not more than 15 kg/cm$^2$(G), preferably 0–10 kg/cm$^2$(G). When a reaction medium which is not vaporized at a reaction temperature and is substantially stable is used, an additional pressure higher than a pressure of carbon dioxide is unnecessarily applied to the reaction system, because a substantial amount of the reaction medium dose not move to a vapor phase and the increase of pressure by the vaporized reaction medium is negligible. Therefore, in such case even when a carbon dioxide gas is introduced into the reaction vessel from the bottom at a conventionally applied pressure, i.e. ambient pressure such as about 0 kg/cm$^2$(G) to be dispersed into the reaction mixture, an objective compound can be obtained at a high yield and a high selective ratio.

The reaction medium may be used, though not restrictively, more than 0.5 times by weight the alkaline metal salts of the phenols or naphthols, more preferably 1–10 times the weight of the salts to be used.

The reaction medium usable in the present invention is, though not restrictively, substantially stable at reaction temperature. That is, a reaction medium having a boiling point higher than the reaction temperature may be usually selected. Using such a reaction medium it does not move to a vapor phase in a substantial amount, so that the content of the alkaline metal salts of phenols or naphthols in the reaction mixture can be maintained constant. However, when the reaction medium having a boiling point close to the reaction temperature is used, the reaction medium may be fed in an amount as much as the amount of the reaction medium removed to the vapor phase.

As a reaction medium there are exemplified aliphatic, alicyclic or aromatic hydrocarbons or ethers having such hydrocarbon residues, for example, light oil, kerosene, gasoline, lubricant oil, white oil, alkylbenzenes, alkylnaphthalenes, diphenyls, diphenylalkanes, alkyldiphenyls, triphenyls, hydrogenated triphenyls, diphenyl ethers, alkylphenyl ethers, alkyl diphenyl ethers, higher alcohols having a high boiling point such as isooctyl alcohol and the like. Mixtures thereof may be, of course, used. A reaction medium having a comparatively high boiling point, e.g. more than 240° C., has merits such as reduction of an energy necessary for the production of hydroxycarboxylic acid and so on, because the evaporation of reaction medium is minimized without substantial change of removing amount of the phenols or naphthols because of the comparatively low steam pressure of the medium.

Following processes are exemplified as a method of removing a part of phenols or naphthols with carbon dioxide to a vapor phase:

(1) A gas in the reaction system is intermittently discharged during the reaction, and carbon dioxide is freshly pressurized into the system;

(2) A gas in the reaction system is continuously discharged during the reaction as a carbon dioxide gas is pressurized into the system so that the pressure in the reaction system may be constantly maintained at the same level. The discharged gas may be wholly or partially used again by circulation. A part of the discharged gas may be exhausted;

(3) A gas in the reaction system is cooled with a condenser connected to the reaction vessel, so that a part of phenols or naphthols is condensed and continuously or intermittently removed from the reaction system. Carbon dioxide gas and the rest of the phenols or naphthols may be collected and returned to the reaction system, if necessary.

In any case, carbon dioxide gas is dispersed into a reaction mixture to progress the reaction as well as the removal of phenols or naphthols out of the reaction system.

The above process may be carried out by any of batch or continuous manners.

During the reaction of alkaline metals salts of phenols or naphthols with carbon dioxide there may be added alkaline metal sources such as alkaline metals carbonate, bicarbonate, alkyl carbonate, alcoholate, alkylate, sulfonate and the like to the reaction mixture.

The finishing of the reaction product may be carried out by a usual manner. For instant, the reaction mixture after the reaction is cooled, and added with water to be separated to an aqueous phase and a reaction medium phase. Unreacted alkaline metal salts of phenols or naphthols as well as free phenols or free naphthols may be collected from the each phase by a usual manner such as control of pH value, separation with acid, extraction with an organic solvent, evaporation under reduced pressure, and the like. The separated unreacted compounds may be used again by recirculation.

The present invention will be illustrated by the following Examples.

EXAMPLE 1

Into an autoclave of 1 liter an aqueous sodium β-naphtholate (50 wt %) 332 g, and hydrogenated triphenyl 388 g were charged and dehydrated at 260° C. for 3 hours as stirring. To the dehydrated mixture hydrogenated triphenyl was additionally added so that the total amount of the hydrogenated triphenyl might be 2.32 times by weight the sodium β-naphtholate (ratio by weight of reaction medium: 2.32). The obtained mixture was further dehydrated at 260° C. for 2 hours, and cooled to 100° C. To the cooled mixture were added β-naphthol 144 g and additional hydrogenated triphenyl in supplemental amount corresponding to the loss during the second dehydration. The resultant was heated to 285° C., into which a carbon dioxide gas was then blown such that the pressure in the reaction system was maintained at 6 kg/cm$^2$ as a gas in the reaction system was discharged from another nozzle accompanied with the carbon dioxide gas at a rate of 2.4 liter/h. The reaction was continued for 3 hours as vaporized β-naphthol and a part of hydrogenated triphenyl were removed out of the reaction system with the discharged carbon dioxide gas, and collected by a condenser.

After the reaction the pressure of the reaction system is reduced to an ambient pressure and the temperature is lowered to 100° C. under a current of nitrogen. The reaction mixture was added with water, heated to 120° C. in a closed system, and then stirred for 30 minutes to decompose by-products. The resultant was cooled, taken out from the autoclave, and separated. The obtained aqueous phase was acidified to give 2-hydroxy-3-naphthoic acid (103.2 g; yield 60%).

EXAMPLE 2

Aqueous solution of potassium phenolate (50% by weight) was prepared in a flask (2 liter) under a nitrogen current. The solution was dehydrated by an evaporator to give a dry powder of potassium phenolate. The potassium phenolate powder obtained 132 g was charged with phenol 35 g and hydrogenated triphenyl 400 g (ratio by weight of reaction medium: 3) into an autoclave (1 liter). After the air in the autoclave was substituted with a nitrogen gas, the reaction mixture was heated at 260° C., and then the nitrogen gas was substituted with a carbon dioxide gas. The inner pressure was increased to 6 kg/cm$^2$ and retained at this level as a carbon dioxide gas was blown into the reaction mixture with stirring and simultaneously discharging a gas in the reaction system containing a carbon dioxide gas, vaporized phenol and hydrogenated triphenol from another nozzle at a rate of 1.2 liter/h. The discharged gas was condensed by a condenser, and the separated carbon dioxide gas was returned to a compressor and recycled into the reaction system. Under the above condition the reaction was continued for 3 hours.

After the reaction the reaction mixture was cooled to 100° C., to which water was added. The mixture was taken out from the reaction vessel, and separated to a water phase and an organic phase. From the separated water phase was extracted with xylene to collect phenol, and then the residual water phase was acidified to separate p-hydroxy benzoic acid (124.2 g, yield 90%).

EXAMPLE 3

Into an autoclave (50 liter) sodium β-naphtholate 8.3 kg, halogenated triphenyl 19 kg (ratio by wei9ht of reaction medium: 2.3) and β-naphthol 7.2 kg were charged. The obtained reaction mixture was heated at 285° C., into which a carbon dioxide gas was then blown such that the pressure in the reaction system was maintained at 6 kg/cm$^2$ as a gas in the reaction system was discharged from another nozzle accompanied with the carbon dioxide gas at a rate of 200 1/min. Into the reaction system a mixture of sodium β-naphtholate and hydrogenated triphenyl which was dehydrated in a similar manner as in Example 1 was continuously charged at a rate of 3.32 kg/h of the former and 6.3 kg/h of the latter, and the surface of the reaction mixture was maintained at the same level by removing the reaction mixture out of the reaction system at a rate of 8-9 kg/h. The above condition was controlled such that the theoretical residence time of sodium β-naphtholate in the reaction system might be 3 hours. The reaction product was separated by batch according to the manner in Example 1. Yield 61%

EXAMPLE 4

Into an autoclave (50 liter) potassium phenolate 6 kg, phenol 1.8 kg and hydrogenated triphenyl 20 kg were charged (ratio by weight of reaction medium: 3.3). Into the reaction mixture a carbon dioxide gas was blown as finely dispersed at 260° C., and the inner pressure was retained at 4 kg/cm$^2$ by discharging a gas in the reaction system with the carbon dioxide gas through another nozzle at a rate of 160 liter/min. A mixed vapor of phenol and hydrogenated triphenyl in the gas was condensed by a condenser. The reaction was continued as the separated carbon dioxide gas was recycled into the reaction system through a compressor, and fresh potassium phenolate and hydrogenated triphenyl were fed into the reaction mixture at a rate of 2 kg/h and 7 kg/h respectively. The reaction product was separated by batch as shown in the Example 2. Yield 91%

EXAMPLES 5-17 (BATCH METHOD)

The reaction was carried out according to the same manner as described in the Example 1 or 2 except that the conditions specifically shown in Table 1 were used. The raw material, conditions, objective compounds and yield were shown in Table 1, in which the molar ratio (A/B) indicates mole of phenols per one mole of alkaline metal salts of phenols or mole of naphthols per one mole of alkaline metal salts of naphthols.

EXAMPLES 18-23 (CONTINUOUS METHOD)

The reaction was carried out according to the same manner as described in the Example 3 or 4 except the conditions specifically shown in Table 2. The results were shown in Table 2.

EXAMPLES 24, 25, COMPARATIVE EXAMPLES 1 AND 2

The reaction was carried out according to the same manner as described in the Example 1 or 2 except the conditions specifically shown in Table 3.

In order to compare a conventional method the Comparative Example 1 (C.1) and Comparative Example 2 (C.2) were made according to the same manner as described in Examples 24 and 25 respectively except that the phenols or naphthols were not removed as a vapor together with the carbon dioxide gas out of the reaction system.

The results were shown in Table 3.

EXAMPLES 26, 27, COMPARATIVE EXAMPLES 3 AND 4

The reaction was carried out according to the same manner as described in the Example 3 except the conditions indicated in Table 4.

The Comparative Example 3 (C.3) was carried out according to the manner described in Japanese Patent Publication No. 9529/1970 (corresponding to U.S. Pat. No. 3,816,521).

The Comparative Example 4 (C.4) was carried out according to the manner described in Japanese Patent Publication No.53296/1981 (corresponding to U.S. Pat. No. 4,239,913).

The results were shown in Table 4.

EXAMPLE 28 (CONTINUOUS METHOD)

2-Hydroxy-3-naphthoic acid is prepared was a 50 liter autoclave according to a similar manner to Example 3 under conditions shown in Table 5. The yield of 2-hydroxy-3-naphthoic acid is determined after 0.25 h and 0.5 h since the reaction starts. The results are shown in Table 5.

COMPARATIVE EXAMPLE 5

The same processes as Example 28 was repeated except that $\beta$-naphthol is not removed with carbon dioxide out of the reaction system as a vapor. The results are shown in Table 5.

TABLE 1

| Ex. No. | raw material | metal | ratio by wt. of reaction medium | reaction temp. °C. | pressure of $CO_2$ kb/cm$^2$ | blowing rate lit./h | reaction time (h) | objective material | yield (%) | molar ratio A/B |
| --- | --- | --- | --- | --- | --- | --- | --- | --- | --- | --- |
| 5 | phenol | K | 3 | 280 | 2 | 6 | 3 | POB | 94 | 0.37 |
| 6 | phenol | K | 1 | 250 | 4 | 2 | 3 | POB | 91 | 0.42 |
| 7 | phenol | K | 1 | 250 | 4 | 2 | 3 | POB | 91.8* | 0.5 |
| 8 | phenol | Na | 2 | 165 | 4 | 0.5 | 2 | SA | 96 | 0.4 |
| 9 | 2,6-diMePh | K | 3 | 260 | 4 | 2 | 3 | 3,5MePOB | 68 | 0.2 |
| 10 | 2-ClPh | K | 3 | 250 | 2 | 2 | 3 | 3ClPOB | 57 | 0.3 |
| 11 | 2-MeOPh | Na | 3 | 250 | 2 | 2 | 3 | 3MeOSA | 82 | 0.3 |
| 12 | 2-AmPh | Na | 3 | 250 | 2 | 2 | 3 | 3NH$_2$SA | 78 | 0.3 |
| 13 | $\beta$-naphthol | Na | 2 | 240 | 2 | 6 | 3 | BON-3 | 50.5 | 1.0 |
| 14 | $\beta$-naphthol | Na | 1 | 240 | 4 | 5 | 3 | BON-3 | 55.2 | 1.0 |
| 15 | $\beta$-naphthol | Na | 1 | 240 | 4 | 10 | 3 | BON-3 | 56 | 1.0 |
| 16 | $\beta$-naphthol | Na | 1 | 240 | 4 | 10 | 3 | BON-3 | 57** | 1.0 |
| 17 | 1-Br $\beta$-naph | Na | 1 | 220 | 4 | 2 | 3 | 1-BrBON-3 | 60 | 1.2 | note:
*K$_2$CO$_3$ (0.2 mol %) was added to potassium phenolate.
**Na$_2$CO$_3$ (0.1 mol %) was added to sodium $\beta$-naphthol.

TABLE 2

| Ex. No. | raw material | metal | reaction medium | ratio by wt. of reaction medium | reaction temp. (°C.) | pressure of $CO_2$ kg/cm$^2$ | blowing rate of $CO_2$ lit./min | feed rate of salt kg/h | residence time (h) | objective material | yield (%) | molar ratio A/B |
| --- | --- | --- | --- | --- | --- | --- | --- | --- | --- | --- | --- | --- |
| 18 | phenol | K | H-TPh | 2 | 260 | 6 | 100 | 15 | 3 | POB | 91 | 0.4 |
| 19 | phenol | K | H-TPh | 1 | 260 | 4 | 200 | 15 | 3 | POB | 90 | 0.5 |
| 20 | phenol | K | light oil | 3 | 260 | 6 | 50 | 4 | 3 | POB | 87 | 0.5 |
| 21 | $\beta$-naphthol | Na | H-TPh | 2 | 260 | 5 | 300 | 18 | 3 | BON-3 | 63 | 1.0 |
| 22 | $\beta$-naphthol | Na | H-TPh | 1 | 260 | 2 | 100 | 10 | 3 | BON-3 | 60 | 0.8 |
| 23 | phenol | Na | H-TPh | 2.6 | 165 | 4 | 50 | 20 | 2 | SA | 91 | 0.3 |

TABLE 3

| Ex. No | raw material | metal | reaction medium | ratio by wt. of reaction medium | reaction temp. °C. | pressure $CO_2$ kg/cm$^2$ | feed amount of salt (g) | molar ratio A/B | reaction temp. (h) | blow rate of $CO_2$ (lit./h) | objective material | yield |
| --- | --- | --- | --- | --- | --- | --- | --- | --- | --- | --- | --- | --- |
| C.1 | phenol | K | light oil | 5 | 230 | 10 | 200 | 0.84 | 1 | — | POB | 75.2 |
| 24 | phenol | K | light oil | 5 | 230 | 10 | 200 | 0.84 | 1 | 5 | POB | 86.1 |
| C.2 | $\beta$-naphthol | Na | light oil | 2.6 | 260 | 3 | 400 | 1 | 3 | — | BON-3 | 43.2 |
| 25 | $\beta$-naphthol | Na | light oil | 2.6 | 260 | 3 | 400 | 1 | 3 | 5 | BON-3 | 53.6 |

TABLE 4

| Ex. | raw material | metal | reaction medium | ratio by wt. of reaction medium | reaction temp. (°C.) | pressure of $CO_2$ kg/cm$^2$ | feed rate of salt kg/h | X kg/h | residence time (h) | blow rate of $CO_2$ (l/min) | molar ratio A/B | objective material | yield (%) |
|---|---|---|---|---|---|---|---|---|---|---|---|---|---|
| C.3 | Ph | K | light oil | 4 | 230 | 5 | 20 | 14 | 1 | — | 0.7 | POB | 71.2 |
| 26 | Ph | K | H-TPh | 4 | 230 | 5 | 20 | — | 1 | 150 | 0.7 | POB | 88.3 |
| 27 | Ph | K | H-TPh | 2 | 200 | 5 | 20 | — | 1 | 150 | 0.7 | POB | 72.0 |
| C.4 | β-Naph | Na | light oil | 1.5 | 270 | 3 | 16.6 | 14.4 | 4.5 | — | 1 | BON-3 | 45.4 |
| 28 | β-Naph | Na | H-TPh | 1.5 | 270 | 3 | 16.6 | — | 4.5 | 100 | 1 | BON-3 | 62.5 |
| 29 | β-Naph | Na | H-TPh | 1.5 | 270 | 0.15 | 16.6 | — | 4.5 | 100 | 1 | BON-3 | 46.0 |

X: amount of phenols or naphthols fed an hour.

TABLE 5

| Ex No. Comp. Ex No. | reaction medium | ratio by wt. of reaction medium | reaction temp. °C. | pressure of $CO_2$ kg/cm$^2$ | molar ratio A/B | blow rate of $CO_2$ (lit./h) | feed of BN-Na kg/h | yield (%) 0.25 h | of BON-3 0.5 h |
|---|---|---|---|---|---|---|---|---|---|
| 28 | light oil | 1.2 | 270 | 3 | 0.5 | 250 | 16.6 | 20.8 | 35.9 |
| Comp. 5 | light oil | 1.2 | 270 | 3 | 0.5 | — | 16.6 | 14.0 | 16.2 |

In Tables 1–5 the abbreviations represent following means:
2,6-diMePh: 2,6-dimethylphenol,
2-ClPh: 2-chlorophenol,
2-MeOPh: 2-methoxyphenol
2-AmPh: 2-aminophenol,
1-Br β-naph: 1-bromo-β-naphthol,
Ph: phenol,
β-Naph: β-naphthol,
H-TPh: hydrogenated triphenyl
POB: p-hydroxy benzoic acid,
SA: salicylic acid,
3,5MePOB: 3,5-dimethyl-4-hydroxy benzoic acid,
3ClPOB: 3-chloro-4-hydroxy benzoic acid,
3MeOSA: 3-methoxy-2-hydroxy benzoic acid,
3NH$_2$SA: 3-amino-2-hydroxy benzoic acid,
BON-3: 2-hydroxy-3-naphthoic acid,
1BrBON-3: 2-hydroxy-1-bromo-3-naphthoenic acid
ratio by weight of reaction medium: ratio by weight of reaction medium to alkaline metal salts of phenols or naphthols,
molar ratio: A/B
A: mole of added phenols or naphthols,
B: mole of alkaline metal salts of phenols or naphthols to be charged.
yield: calculated based on alkaline metal salts of phenols or naphthols.

What is claimed is:

1. In a process for production of an aromatic hydroxycarboxylic acid which comprises reacting alkaline metal salts of phenols or naphthols selected from the group consisting of sodium phenolates, potassium phenolates, sodium α-naphtholates, potassium α-naphtholates, and sodium β-naphtholates, with carbon dioxide under such a condition that said alkaline metal salts of phenols or naphthols are melted in the presence of a reaction medium, the improvement which comprises removing by-products such as phenols or naphthols by discharging, during the reaction, $CO_2$ gas which contains vapor of the by-products out of the reaction vessel.

2. A process for production of an aromatic hydroxycarboxylic acid of the claim 1, in which the reaction medium is selected from hydrocarbons or ethers having a boiling point of more than 150° C.

3. A process for production of an aromatic hydroxycarboxylic acid of the claim 1, in which the reaction is carried out in a reaction mixture containing phenols or naphthols, the alkaline metal salts as described in the claim 1, and the reaction medium.

4. A process for production of an aromatic hydroxycarboxylic acid of claim 3, in which a molar ratio of the phenols or naphthols to the alkaline metal salts of the phenols or naphthols in a reaction mixture is from 0.1 to 3.

5. A process for production of an aromatic hydroxycarboxylic acid of claim 1, in which the reaction is carried out under a pressure of 0–10 kg/cm$^2$ by a carbon dioxide gas.

6. A process for production of an aromatic hydroxycarboxylic acid of claim 1, in which the reaction is carried out by dispersing the carbon dioxide gas into a reaction mixture, and removing gaseous by-products together with the carbon dioxide gas.

7. A process for production of an aromatic hydroxycarboxylic acid as in claim 1, wherein the discharge gas is condensed by a condenser to separate carbon dioxide and the carbon dioxide gas is circulated into the reaction vessel.

8. A process for production of an aromatic hydroxycarboxylic acid as in claim 1, wherein the by-products include phenols or naphthols.

* * * * *